US008361460B2

(12) United States Patent
Morimatsu et al.

(10) Patent No.: US 8,361,460 B2
(45) Date of Patent: Jan. 29, 2013

(54) FOOD ALLERGENS, METHOD OF DETECTING FOOD ALLERGENS AND METHOD OF DETECTING FOOD ALLERGY-INDUCING FOODS

(75) Inventors: Fumiki Morimatsu, Tsukuba (JP);
Yoshihisa Takahata, Tsukuba (JP);
Takashi Matsumoto, Tsukuba (JP);
Izumi Miyazawa, Tsukuba (JP);
Muneshige Shimizu, Tsukuba (JP)

(73) Assignee: Nippon Meat Packers, Inc., Osaka-shi, Osaka (JP)

( * ) Notice: Subject to any disclaimer, the term of this patent is extended or adjusted under 35 U.S.C. 154(b) by 165 days.

(21) Appl. No.: 10/488,461

(22) PCT Filed: Sep. 5, 2002

(86) PCT No.: PCT/JP02/09066
§ 371 (c)(1),
(2), (4) Date: Mar. 4, 2004

(87) PCT Pub. No.: WO03/022876
PCT Pub. Date: Mar. 20, 2003

(65) Prior Publication Data
US 2004/0265234 A1 Dec. 30, 2004

(30) Foreign Application Priority Data
Sep. 5, 2001 (JP) .................................. 2001-269592

(51) Int. Cl.
*A61K 39/395* (2006.01)
*C07K 16/00* (2006.01)

(52) U.S. Cl. ............... 424/130.1; 424/171.1; 530/387.1; 530/389.1

(58) Field of Classification Search ........................ None
See application file for complete search history.

(56) References Cited

FOREIGN PATENT DOCUMENTS

| EP | 784931 A2 | 7/1997 |
|---|---|---|
| EP | 0 794 434 A1 | 10/1997 |
| EP | 0 981 050 A1 | 2/2000 |
| JP | 9-136897 A | 5/1997 |
| JP | 10-191935 A | 7/1998 |
| WO | WO 97/11368 | 3/1997 |
| WO | WO 97/11368 A1 | 3/1997 |
| WO | WO 97/24139 A1 | 7/1997 |

OTHER PUBLICATIONS

Egger et al. 'Controlled trial of hyposensitization in children with food-induced hyperkinetic syndrome.' Lancet. 339:1150-1153.*
Ermel et al. 'The atopic dog A model for food allergy.' Laboratory Animal Science. 47(1):40-49, 1997.*
Yeung et al. 'Enzyme Immunoassay for determination of peanut proteins in food products.' J. AOAC INt. 79(6):1411-1416, 1996.*
Lerner et al. 'Tapping the immunological repertoire to produce antibodies of predetermined specificity.' Nature. 299:592-596, 1982.*
Perry et al. 'The relationship of allergen-specific IgE levels and oral food challenge outcome.' J. Allergy. Clin. Immunol. 114:144-149, 2004.*
Pizzano et al. 'Immunochemical evaluation of bovine beta-casein and its 1-28 phosphopeptide in cheese during ripening.' J. Agric. Food. Chem. 48:4555-4560, 2000.*
Blumenthal et al. 'Definition of an Allergen.' Allergens and Allergen Immunotherapy. Ed. R Lockey, S. Bukantz and J. Bousquet. New York: Marcel Decker, 2004.37-50.*
Egger et al. 'Controlled trial of hyposensitization in children with food-induced hyperkinetic syndrome.' Lancet. 339:1150-1153, 1992.*
M. Besler et al., "Immunological Characterization of Egg White Allergens Collected by Capillary Electrophoresis", Food and Agricultural Immunology, 1998, vol. 10, pp. 157 to 160.
J.M. Wal et al., "Enzyme Immunoassay of Specific Human IgE to Purified Cow's Milk Allergens", Food and Agricultural Immunology, 1995, vol. 7, pp. 175 to 187.
Becker, W.M. et al. Journal of Chromatography, May 25, 2001, pp. 131-140 vol. 756, No. 1-2.
Besler, Matthias et al. Journal of Chromatography, May 25, 2001, pp. 207-228, vol. 756, No. 1-2.
Kaifa, °Protein Allergens in Foods and Detection Thereof, Food Research and Development, vol. 21, No. 2, Apr. 2000, pp. 49-50.
De Jong, E. C., et al, "Identification and partial characterization of multiple major allergens in peanut proteins," Clinical and Experimental Allergy, 1998, vol. 28, pp. 743-751.
Acosta et al., "Production and Characterization of Rabbit Polyclonal Antibodies to Almond (*Prunus dulcis* L.) Major Storage Protein", Journal of Agricultural and Food Chemistry, vol. 47, No. 10, 1999, pp. 4053-4059.
Hlywka et al., "A Sandwich Enzyme-Linked Immunosorbent Assay for the Detection of Almonds in Foods", Journal of Food Protection, vol. 63, No. 2, 2000, pp. 252-257.
Holzhauser et al., "Indirect Competitive ELISA for Determination of Traces of Peanut (*Arachis hypogaea* L.) Protein in Complex Food Matrices", Journal of Agricultural and Food Chemistry, vol. 47, No. 2, pp. 1999, 603-611.
Kim et al., "Isolation of rice allergenic cDNA clones from a rice cDNA library by immunoscreening with a polyclonal antibody specific to 16 kD rice allergenic protein", Experimental and Molecular Medicine, vol. 31, No. 4, Dec. 1999, pp. 185-190.

(Continued)

*Primary Examiner* — Nora Rooney
(74) *Attorney, Agent, or Firm* — Birch, Stewart, Kolasch & Birch, LLP.

(57) ABSTRACT

The present invention provides a method for detecting food allergens, antibodies and antigens to prepare the antibodies. The antigens of this invention are a mixture comprising multiple native and/or heated food allergens that IgE antibodies of food-allergy patients recognize. The antibodies of this invention are prepared by immunizing animals with the above-mentioned antigens. The food allergen-detecting method of this invention relates to the above-mentioned antibodies. As the method can detect food allergens and food allergy-inducing foods, it can provide safety to food allergy patients.

35 Claims, 2 Drawing Sheets

OTHER PUBLICATIONS

Koppelman et al., "Comparison of different immunochemical methods for the detection and quantification of hazelnut proteins in food products", Journal of Immunological Methods, vol. 229, 1999, pp. 107-120.

Leduc et al., "Immunochemical detection of egg-white antigens and allergens in meat products", Allergy, vol. 54, 1999, pp. 464-472.

Plebani et al., "Monoclonal and polyclonal antibodies against casein components of cow milk for evaluation of residual antigenic activity in 'hypoallergenic' infant formulas", Clinical and Experimental Allergy, vol. 27, 1997, pp. 949-956.

Yeung et al., "Determination of Egg Proteins in Food Products by Enzyme Immunoassay", Journal of AOAC International, vol. 83, No. 1, 2000, pp. 139-143.

\* cited by examiner

Figure 1

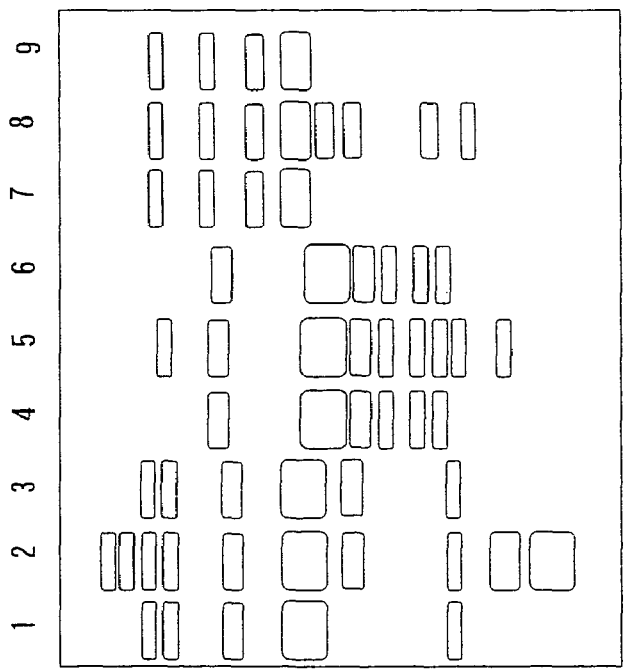

1 ; Reaction between standard egg antigen and pooled patient serum
2 ; Reaction between the standard egg antigen and rabbit anti-standard egg antigen antibody
3 ; Reaction between the standard egg antigen and rabbit anti-standard egg antigen-fraction antibody
4 ; Reaction between standard milk antigen and the pooled patient serum
5 ; Reaction between the standard milk antigen and rabbit anti-standard milk antigen antibody
6 ; Reaction between the standard milk antigen and rabbit anti-standard milk antigen-fraction antibody
7 ; Reaction between standard wheat antigen and the pooled patient serum
8 ; Reaction between the standard wheat antigen and rabbit anti-standard wheat antigen antibody
9 ; Reaction between the standard wheat antigen and rabbit anti-standard wheat antigen-fraction antibody

FOOD ALLERGENS, METHOD OF DETECTING FOOD ALLERGENS AND METHOD OF DETECTING FOOD ALLERGY-INDUCING FOODS

BACKGROUND OF THE INVENTION

The present invention relates to a mixture comprising multiple native and/or denatured food allergens recognized by IgE antibodies of food-allergy patients, antibodies prepared by immunizing an animal with the mixture and a method for detecting the food allergens and allergy-inducing foods that involves using said antibodies. The invention provides safety to food allergy patients, since it is useful for understanding mechanisms of food-allergy onset, developing and verifying hypoallergenic foods, and detecting food allergens in foods, their raw materials and such food-manufacturing environments as food-manufacturing machines and processes.

Food allergy is a detrimental immunoreaction in susceptible individuals that is caused by ingestion of an allergy-inducing substance in a food (referred to as a food allergen in the following). The food allergy can cause dermatitis, asthma, digestive-tract obstacle, anaphylaxis shock, etc. Allergies are classified into types I to IV, depending on the mechanism of disease onset. Food allergy is primarily type-I allergy, in which IgE antibodies react with food allergens taken inside the body. The number of food-allergy patients has been increasing in recent years. Such a phenomenon causes serious problems in the fields of medical science and in the food industry.

To prevent such a hazard, it is necessary to provide information to the consumers through labeling. An FAO/WHO joint food standard committee (Codex Alimentarius Commision) has recognized the necessity of labeling of foods containing any of eight raw materials known as food allergens, and advised each of the member nations to implement the labeling system (June, 1999). In Japan, the labeling of 24 items was promulgated in consideration of the severity and frequency of food allergies (enforced since April, 2002). It should be noted that these regulations require the labeling of neither allergenic substance nor food allergen itself but that of food containing the allergenic substance and food allergen, namely allergy-inducing foods.

Allergy-inducing foods include eggs, milk, meat, fishes, the crustaceans and mollusks, cereals, legumes and nuts, fruits, vegetables, beer yeast, or gelatin. Similarly, ovoalbumin, ovomucoid, lysozyme, casein, beta-lactoglobulin, alpha-lactoalbumin, gluten, alpha-amylase inhibitor, etc. are known as allergy-inducing foods.

Furthermore, (1) regardless of present knowledge, it is conceivable that there are other many foods and ingredients (food allergens) that cause food allergy; (2) the allergy-inducing foods and ingredients (food allergens) are diverse and reactions to these allergens differ among food allergy patients; and (3) as the after-mentioned examples show, many known and unknown allergens exist even in a single allergy-inducing food. No conventional method, however, can easily detect so many allergy-inducing foods or food allergens.

Foods are prepared by such processes as heating, freezing, drying, salting, fermentation, enzymatic treatment, etc. (referred to as food-manufacturing processes in the following) to improve and stabilize their digestibility, shelf lives, taste, physical properties, etc. Although the food-manufacturing processes affect proteins and modify their molecular structures (e.g., denaturation of protein), it has seldom been discussed whether or not such food-manufacturing processes cause the formation of food allergens.

The present invention elucidated the following facts: (1) some heated food ingredients express allergenicity; (2) allergy-inducing components or epitopes of an individual allergy-inducing food may be altered, depending on whether the concerned food is heated or not. Namely, a) non-heated egg antigen, b) heated egg antigen prepared by heating the antigen in a), c) serum prepared by mixing the pooled serum from multiple food allergy patients (referred to as pooled patient serum) and a) (non-heated egg antigen-depleted serum), and d) serum prepared by mixing the pooled patient serum and b) heated egg antigen-depleted serum) were prepared. From the results of reactions between a) and c) or a) and d) and between b) and c) or b) and d), it was shown that the non-heated egg antigen-depleted serum could not immunologically react with the non-heated egg antigen but could react with the heated egg antigen: similarly, it was shown that the heated egg antigen-depleted serum could not immunologically react with the heated egg antigen but could react with the non-heated egg antigen. In summary, the food allergy patients carry IgE antibodies specific to both processed and non-processed foods, resulting in food allergy. So far, however, no simple method has been available to detect allergens in processed foods or their ingredients.

Methods screening for food allergens in chicken egg, peanut, casein, beta-lactoglobulin and gluten have been commercially available (Food and Development, Vol. 35, p 10-11). However, all or some of them possess one or more the following drawbacks: (1) The methods cannot always detect allergens that food allergy patients are sensitive to. In other words, they cannot always detect substances that are recognized by IgE antibodies of the patients; (2) The methods can detect known allergens, and a single allergen (single antigen) per method; (3) The methods using single antigen-detecting antibodies are not applicable to foods with inhibitory substances; (4) The methods using single antigen-detecting antibodies cannot exactly quantify the allergy-inducing foods as shown in the after-mentioned examples; (5) The methods using single antigen-detecting antibodies are not applicable to inspection of allergy-inducing foods containing no antigen (e.g., a method using a single antibody prepared by exposure to ovalbumin localized in egg white is not applicable to inspection of egg yolk, egg yolk mayonnaise, etc. and it is known that food allergy is caused by egg yolk); (6) The methods using single antigen-detecting antibodies are not applicable to inspection of the processed foods, because they cannot detect denatured or molecule-modified allergens; and (7) Monoclonal antibodies against native and denatured beta-lactoglobulin, ovoalubmin and alpha-casein have been reported (Allergy, vol. 50, p 309). Their usefulness may decrease, if the epitopes are removed or modified by the food-manufacturing processes, because the monoclonal antibodies only detect individual epitopes in a food-allergen molecule.

Although methods screening for food allergens using sera from patients who are allergic to rice (Japanese Patent Disclosure 2000-65820), egg and milk (Japanese Meat Science, vol. 39, p 166-169) have been reported, they are useful in hospitals but not in inspection organizations nor in food manufacturing factories, because the methods need a lot of sera from the patients. Although a food-allergen detection method depending on anaphylaxis reactions has been reported (FFI J., No. 180, p 77-82), it is not useful in most of the food-manufacturing factories because of complicated methodology and laboratory-animal husbandry. Although methods using flow system and enzyme-labeled antibodies and allergen sensors using microelectrodes have been developed (Japanese Food Industry, Vol. 42, p 53-56), many problems need to be solved before these methods can be put into practical use.

DISCLOSURE OF THE INVENTION

The present invention was accomplished to solve problems of conventional methods as mentioned above. The purposes of this invention are to supply (1) a mixture comprising multiple known and/or unknown as well as native and/or denatured food allergens that can be recognized by IgE antibodies of food-allergy patients (referred to as the first invention of this invention for convenience), (2) antibodies prepared by immunizing an animal with the mixture (referred to as the second invention of this invention), and (3) a method for detecting food allergens and allergy-inducing foods that use said antibodies (referred to as the third invention of this invention).

BRIEF EXPLANATION OF THE DRAWINGS

FIG. 1 shows reactions between a standard antigen and patients' IgE antibodies and those between the standard antigen and an antibody against standard-antigen antibody of this invention.

THE BEST MODE FOR APPLYING THE INVENTION

Figure 2:
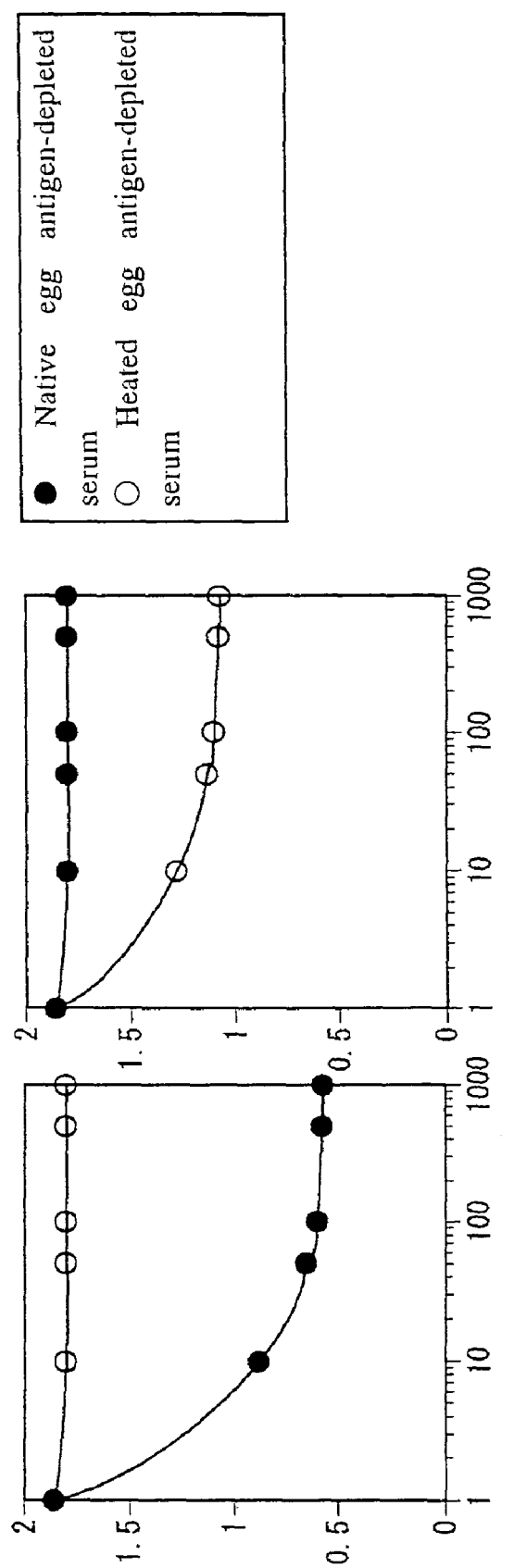
FIG. 2 shows that patient serum carries IgE antibodies specific to both native and denatured egg proteins.

The first invention of this invention is accomplished by
(1-i) isolating IgE antibodies from pooled serum of the food-allergy patients, and
(1-ii) separating multiple substances recognized by the above-mentioned IgE antibodies (in other words, multiple food allergens that IgE antibodies of the food allergy patients recognize) from foods or their ingredients (collectively referred to as foods in the following) treated with or without food-manufacturing processes by using such immunological methods as affinity chromatography and immunoprecipitation.

The first invention of this invention is also accomplished by
(2-i) conventionally carrying out SDS-PAGE of the food ingredients and transferring to a membrane,
(2-ii) carrying out western blotting using the membrane, pooled patients' serum, a conjugated antibody against human IgE and a chromogenic reagent (in other words, preparing a profile of multiple food allergens that IgE antibodies of the food allergy patients recognize),
(2-iii) similarly, carrying out western blotting using the membrane, animal serum prepared by conventionally immunizing the food ingredients, a conjugated anti-animal IgG and the chromogenic reagent, and then
(2-iv) comparing both western-blotting profiles, and measuring molecular sizes of bands shown not in the former but in the latter (in other words, multiple substances that IgE of the food-allergy patients cannot recognize), and
(2-v) depending on the above-mentioned results, separating multiple food allergens that IgE antibodies of the food-allergy patients can recognize from food ingredients by such a conventional method as gel-filtration chromatography.

The second invention of this invention is animal antibodies against food allergens prepared by immunizing an animal with the multiple food allergens (including those processed and/or not processed) that are prepared by the above-mentioned first invention and that can be recognized by IgE antibodies of the food-allergy patients (referred to as antibodies recognizing the multiple antigens).

The third invention of this invention is a method for detecting the food allergens and allergy-inducing foods characterized by using the antibodies recognizing the multiple antigens.

Temperature ranges of heat treatment in the above-mentioned food-manufacturing processes are equivalent to those of food-manufacturing processes, preferably between 40 and 250 degree Celsius and more preferably between 60 and 120 degree Celsius. The antigens are prepared by mixing a raw antigen and antigens heated at two to six different temperatures. The food-allergen fractions that can be recognized by the food-allergy patients' IgE antibodies are prepared from the mixture with the first invention of this invention and subjected to immunization of animals.

If a target of the detection is restricted to a heated food, the food-allergen fractions that the food-allergy patients' IgE antibodies recognize are prepared from the heated food with the first invention of this invention and subjected to immunization of animals.

Examples of animals to be immunized are rabbits, goats, sheep, rats, mice, guinea pigs, horses, pigs, chicken, etc. During an immunization period, it is desirable to partially collect blood and check titers of the anti-food allergen antibody. The antibodies of this invention may be either monoclonal or polyclonal. As the after-mentioned examples show, multiple known and unknown food allergens that IgE antibodies of the food-allergy patients recognize exist even in a single food-allergy inducing food. The polyvalent antibodies recognizing multiple food allergens, i.e., the antibodies recognizing multiple antigens, can easily be prepared by immunizing the animals with these multiple food allergens.

As animal antibodies against the food allergens that the food allergy patients' IgE antibodies recognize, anti-sera of the animals can be used as they are. The anti-sera can be used after absorption treatment with the fractions that cannot be recognized by the food allergy patients' IgE antibodies and after conventional IgG purification.

The method for detecting the food allergens and food allergy-inducing foods of this invention is applicable to foods containing the allergens without any restriction. Examples of the allergy-inducing foods are eggs, milk, meat, fishes, crustacea and mollusks, cereals, legumes and nuts, fruits, vegetables, beer yeast, and gelatin. More particularly, egg white and egg yolk of the eggs, milk and cheese of the milk, pork, beef, chicken and mutton of the meat, mackerel, horse mackerel, sardine, tuna, salmon, codfish, flatfish and salmon caviar of the fishes, crab, shrimp, blue mussel, squid, octopus, lobster and abalone of the crustacea and mollusks, wheat, rice, buckwheat, rye, barley, oat, corn, millet, foxtail millet and barnyardgrass of the cereals, soybean, peanut, cacao, pea, kidney bean, hazelnut, Brazil nut, almond, coconut and walnut of the legumes and nuts, apple, banana, orange, peach, kiwi, strawberry, melon, avocado, grapefruit, mango, pear, sesame and mustard of the fruits, tomato, carrot, potato, spinach, onion, garlic, bamboo shoot, pumpkin, sweet potato, celery, parsley, yam and Matsutake mushroom of the vegetables, the foods containing them, and the ingredients thereof (e.g., ovoalbumin, ovomucoid, lysozyme, casein, beta-lactoglobulin, alpha-lactoalbumin, gluten, and alpha-amylase inhibitor). These foods may be processed by heating, freezing, drying, salting, fermentation, enzymatic processing, etc.

Generally, allergens that food allergy patients' IgE antibodies can recognize with 50% or more of probability are called major allergens, otherwise minor ones. Food allergy is caused not only by major allergens but also minor ones. Some patients are not sensitized by the major allergens but the minor ones. Therefore, the method screening for food allergens should detect both major and minor allergens. The screening method of this invention can detect both native and denatured multiple allergens that the food allergy patients recognize.

To prepare the antibodies satisfying such requirements, the present inventors studied and found out the following.

Namely, the food ingredients were conventionally subjected to SDS-PAGE analysis and the gel was transferred on a membrane:
(i) Western blotting was carried out with the membrane, the pooled patient serum, a conjugated anti-human IgE antibody and a chromogenic reagent;
(ii) Similarly, western blotting was done with the membrane, serum prepared by conventionally immunizing the food ingredients to animal, a conjugated anti-animal IgG antibody and the chromogenic reagent;
(iii) From comparison of both western-blotting profiles, the following were observed; (1) there were bands commonly stained in both membranes, (2) there were the bands stained not in the former but in the latter (in other words, multiple non-allergenic substances recognized by the food-allergy patients' IgE), and (3) the bands stained only in the latter distributed at higher and/or lower molecular-weight positions than the bands stained in the former; and
(iv) From the above-mentioned results, multiple food-allergen fractions that the food-allergy patients' IgE antibodies could recognize were isolated from the food ingredients by gel-filtration chromatography and immunized to animals to prepare the antibodies against the multiple food allergens. Such homoiothermal animals as rabbits, goats, sheep, rats, mice, guinea pigs, horses, pigs, and chicken might be immunized. Any of the immunization methods known among those skilled in the art might be adopted.

The antibodies prepared as mentioned above can be used for the food allergen-detection method of this invention. The antibodies may be immobilized on a microtiter plate, a PVDF membrane, a nitrocellulose membrane, a chromatostrip, a test tube, a bead, a nylon membrane, etc., and applied to such immunological methods as enzyme immunoassay, immunoblotting, dot blotting, immunochromatography and antibody chip.

As mentioned above, the food allergen-detection method of this invention aims at detecting the multiple food allergens in foods and such environments as food-manufacturing machines and processes. Liquid extracts from the foods are preferably used for assay. Although extractants are preferably water, phosphate-buffered saline, Tris-HCl buffer, alcohol, etc., they are not limited to these as far as the allergens can be extracted. To improve the efficiency of extraction of the allergens from foods, a protein denaturation agent (e.g., SDS or urea), an SH-containing antioxidant (e.g., 2-mercaptoehanol), etc. can be added to the extractants, if necessary. The multiple allergens existing in such food-manufacture environment as machines and processes can be determined with the liquid taken by wiping (swabbing) the environment and that taken by trapping air of the environment in a washing bottle.

As far as the principle of the food allergen-detection method of this invention is such immunological methods as enzyme immunoassay, immunoblotting and fluorescent multiple-immunobead method, they are not limited to a specific method. For example, sandwich ELISA, the competitive method, direct method, etc. are examples of enzyme immunoassay. If the antibodies are labeled, enzymes (e.g., peroxidase, alkali phosphatase and beta-galactosidase), fluorescent substances (e.g., fluorescent isothiocyanate), biologically-luminescent substances (e.g., luciferin-luciferase), chemically-luminescent substances (e.g., luminol, an acridine derivative and an adamantane derivative), biotin, avidin, a gold colloid, radioactive materials (e.g., $^{32}P$), etc. can be used.

Outlines of the procedures of sandwich ELISA, competitive method and direct method are explained in the following as examples of the detection method of this invention.

To carry out the sandwich ELISA, labeled antibodies recognizing the multiple allergens (those recognizing multiple antigens) of this invention are prepared. Non-labeled antibodies recognizing the multiple antibodies of this invention are immobilized on an ELISA plate by adsorption or chemical binding. Next, the area of the plate where the antibodies are not immobilized is blocked with protein that does not interfere the reaction system; e.g., gelatin and rabbit serum albumin. The extracts from the foods, the food ingredients or the food-manufacturing environments (henceforth called samples) or the standard antigen are added to the plate to carry out the first antigen-antibody reaction. After the reaction, the plate is washed. To carry out the second antigen-antibody reaction, above-mentioned labeled antibodies are added to the plate, where the immobilized antibodies capture the allergens. After washing and removing the excess labeled antibodies, the detection reagent (e.g., 1,2-phenyldiamine and $H_2O_2$ in a case of peroxidase and p-nitrophenylphosphate in the case of alkali phosphatase) is added. The allergens are detected or quantified by determining amounts of reactants between the label and the detection reagent.

A calibration curve can be obtained by changing added amounts of the standard antigen or food allergy-inducing food (e.g. egg and milk) on the ELISA plate. The amounts of the food allergens or food allergy-inducing foods can be quantified with the calibration curve. If the quantified value is 1 ppm or more, the sample may be a food allergy-inducing food.

Because a method with single-antigen detecting antibody must convert a value obtained by the single-antigen detecting antibody to a content of an allergy-inducing food, quantification errors may occur.

Taking ovomucoid and avoalbumin for instances as single antigens, concentrations of ovomucoid and avoalbumin in whole egg are approximately 4% and 2%, respectively. Those in egg white are approximately 8% and 4%, respectively. However, egg yolk contains neither ovomucoid nor avoalbumin. Accordingly, (1) a method only detecting either ovomucoid or avoalbumin is not applicable for the determination of an egg-yolk protein; (2) if a calibration curve prepared by whole egg is applied to the determination of egg white, twice or more values than actual ones are quantified; and (3) if the actual values excess a quantification range, extremely high quantitative is values are determined.

Similarly, it is a problem that single antigen-recognizing antibody cannot precisely quantify processed milk fortified with sodium caseinate, whey protein, etc., since concentrations of casein and beta-lactogloblin in whole milk protein are approximately 80% and 10%, respectively.

The multiple antigen-recognizing antibodies of this invention, however, possess no or less such a problem.

With the competitive method, a given quantity of a standard antigen is directly immobilized on a solid phase, which is blocked with a non-reactive protein. Then, an enzyme-conjugated antibody recognizing allergen and a sample are simultaneously added to the plate. The plate is allowed to stand for a given time and washed to remove non-bound substances. A color-developing substrate is added to the plate and then the reaction is stopped. The reaction between the immobilized allergen and the enzyme-conjugated antibody treated with the sample in advance can be detected.

With the direct method, a sample is directly adsorbed on the solid phase, which is blocked with a non-reactive protein and reacted with an enzyme-conjugated antibody recognizing the allergen. Then, the same procedures as mentioned above are applied to detect the allergen in the sample.

With any of above-mentioned sandwich ELISA, competitive and direct methods, fluorescent, biologically- and chemically-luminescent substrates can be used for color development. According to the purpose, nature of the sample, principle, etc. of the determination, those skilled in the art can modify other conditions of the methods of this invention.

The method for detecting the food allergen of this invention can sensitively detect 0.1 or 1.0 ng/ml or more allergens in extracts from foods and their raw materials.

INDUSTRIAL APPLICABILITY

The mixture comprising multiple native and/or denatured food allergens recognized by IgE antibodies of food-allergy patients and the antibodies of this invention are useful for understanding the mechanism of onset of food allergy and developing technology to reduce allergenicity of a food allergen. The method for detecting food allergen of this invention is useful for verifying utility of hypoallergenic technology and detecting the food allergens in foods, food allergy-inducing foods and such food-manufacturing environment as food-manufacturing machines and processes. Accordingly, the present invention is useful for providing safety to the food-allergy patients and solving medical and industrial problems caused by recent increment of the number of the food-allergy patients.

EXAMPLES

This invention is explained more concretely based on the following Examples but they should not be construed as limiting the scope of this invention. Abbreviations in this specification are those commonly used in the technical field.

Example 1

Preparation of Standard Antigens of Various Foods (1) Chicken, Quail and Duck Eggs One-kg chicken eggs were shelled, homogenized, freeze-dried and finely ground to prepare a standard chicken-egg antigen. After 10-g antigen was suspended in 10-fold volume of phosphate-buffered saline, pH 7.0 (abbreviated to PBS in the following), and then dispensed into 5 test tubes, which were not heated or heated for 30 min at 60, 80, 100 and 120 degree Celsius, respectively. Then, they were mixed together and homogenized to prepare the sample. Similarly, the samples were prepared with quail and duck eggs.

(2) Cow Milk

One-litter milk was agitated with cooling to solidify and precipitate milk fat, which was filtered through absorbent cotton. After repeating such a procedure 3 times, the filtrate was freeze-dried and then finely ground to prepare a standard cow-milk antigen. Similarly, the sample was prepared as described in (1).

(3) Wheat and Rice

One-kg wheat flour was extracted with 5-fold amount of 4 M urea-added 0.1 M Tris-HCl buffer (pH 8.6) with agitation for 2 h at room temperature, and then centrifuged. Supernatant was dialyzed, freeze-dried and then finely ground to prepare a standard wheat antigen. Similarly, the sample was prepared as described in (1). Similarly, the sample was prepared from rice flour.

(4) Buckwheat

One-kg buckwheat flour was extracted with 5-fold amount of 1% NaCl-added 0.1 M Tris-HCl buffer (pH 8.4) with agitation for 2 h at room temperature, and then centrifuged. Supernatant was dialyzed, freeze-dried and then finely ground to prepare a standard buckwheat antigen. Similarly, the sample was prepared as described in (1).

(5) Peanut

One-kg peanut was ground and defatted with 5-fold amount of n-hexan with agitation for 2 h at room temperature. After repeating such a procedure 3 times and then removing n-hexane, the preparation was extracted with 5-fold amount of 1% NaCl-added 0.1 M Tris-HCl buffer (pH 8.4) with agitation for 2 h at room temperature, and then centrifuged. Supernatant was dialyzed, freeze-dried and then finely ground to prepare a standard peanut antigen. Similarly, the sample was prepared as described in (1).

(6) Soybean

A standard soybean antigen was prepared as described in (5). Similarly, the sample was prepared as described in (1).

Example 2

Various Purified Food Allergens (1) Purified Chicken-Egg Allergen

Ovoalbumin, a major allergen of chicken egg, was suspended in 10-fold volume of PBS, pH 7.0, and dispensed into 5 test tubes, which were not heated or heated for 30 min at 60, 80, 100 and 120 degree Celsius, respectively. Then, they were mixed together and homogenized to prepare the sample. Similarly, a sample of ovomucoid was prepared. It is known that ovoalbumin and ovomucoid are proteins localized in egg white.

(2) Purified Cow-Milk Allergen

Similarly as described in Example 2 (1), the samples of casein, beta-lactoglobulin and alpha-lactoalbumin were prepared. It is known that beta-lactoglobulin and alpha-lactoalbumin are proteins localized in milk whey.

Example 3

Preparation of Antibody (1) Preparation of Rabbit Antibodies Against Various Standard Food Antigens Each sample prepared in Example 1 was emulsified with Freund's complete adjuvant (used for the first immunization) and incomplete one (used for the second and thereafter immunization) and subjected to immunization of Japanese white rabbits 4 to 6 times. In the meantime, blood was partially collected to confirm production of antibody against the antigen, and then all the blood was collected. Thus, the antibodies were prepared.

(2) Preparation of Antibodies Against Various Purified Food Antigens

Similarly, antibodies against various purified food allergens were prepared as described above.

Example 4

Detection of Various Food Allergens by the Immunoblotting Method (1) Pooled Serum of Patients and Rabbit Antibodies Pooled serum was prepared by mixing equal amount of serum from 20 patients with RAST (radioallergosorbent test) scores of two or more (specific IgE antibody >0.7 UA/ml) against egg, milk or wheat. The rabbit antibodies against egg, milk and wheat were those prepared in Example 3 (1).

(2) Sodium Dodecyl Sulfate-Polvacrylaminde Gel Electrophoresis (SDS-PAGE)

The above-described standard egg, milk and wheat antigens were heated with 2-mercaptoethanol for 3 min and electrophoresed in a mini slab gel of 10% concentration. The gel was electrically transferred on a PVDF. (polyvinilidene difluoride) membrane. Apart of the membrane was subjected to detection of protein with a gold colloid staining kit (BioRad).

(3) Immunostaining

The above-mentioned PVDF membrane was blocked with 1% human serum albumin (HSA). Next, the membrane was washed with PBS containing 0.05% Tween 20 (PBST), reacted with the pooled patients' serum (100-fold dilution) or the rabbit antibody (1000-fold dilution) for 2 h at room temperature, washed, and then reacted with a secondary antibody of alkali phosphatase-conjugated anti-human IgE-$\epsilon$ chain goat antibody (2500-fold dilution) or alkali phosphatase-conjugated anti-rabbit IgG antibody (4000-fold dilution) for 1 h at room temperature. The membrane was washed with PBST, reacted with a chemiluminescent substrate of 4-methyl-4(3-phosphatephenyl)spiro[1,2-dioxetane-3,2-adamantane]disodium salt (Lumi-Phos 530, Wako Pure Chemical) for 30 min at room temperature and exposed on a photosensitive film to detect photons produced by dephospholization reaction of the alkali phosphatase. These results are shown in FIG. 1.

As FIG. 1 shows, the pooled patients' serum produced multiple bands (Lanes 1, 4, and 7 of FIG. 1) and the multiple allergens which the patients' IgE could recognize existed in each food.

Meanwhile, the rabbit antibodies detected the food allergens that the patients' IgE could recognize (Lanes 2, 5, and 8 of FIG. 1).

The substances that both sera recognized were as follows: ovoalbumin, ovomucoid, lysozome and ovotransferrin of the egg; casein, beta-lactoglobulin and alpha-lactoalbumin of the milk; glyadine and alpha-amylase inhibitor of the wheat; 132-, 84-, 27- and 11-kDa substances of the buckwheat; and 107-, 72-, 35- and 28-kDa substances of the peanut.

In addition, the rabbit antibodies did not detect non-food allergens that the patients' IgE could not recognize.

(4) Concentration and Fractionation of Allergens

The antibodies which cannot recognize any substance except for allergens were prepared as follows:

Comparing the molecular-weight distribution of the bands stained by the pooled patients' serum with that by the animal antibodies, it was noticed that some of the bands of the latter distributed at higher and/or lower molecular-weight positions than those of the former (FIG. 1). Fractions equivalent to the molecular weights of the food allergens that the food-allergy patients' IgE recognized were collected from the standard antigen with gel filtration chromatography (named allergen fraction in the following). The sample was prepared as described in Example 1 and subjected to immunization of an animal to prepare the anti-allergen fraction antibodies. From western blotting carried out as mentioned above using the antibodies, it was found that the antibodies generally recognized the food allergens that the pooled patients' serum could recognize Lanes 3, 6, and 9 of FIG. 1).

Such concentration and fractionation of the allergens can be accomplished by immunoprecipitation as well as affinity chromatography using the patients' IgE antibodies and ion-exchange chromatography.

Example 5

Dot-Blot Detection of Major Allergens and their Heated Preparations

After a PBS-soaked PVDF membrane was set in a dot-blotting apparatus, the purified major allergens (ovoalbumin, ovomucoid, ovotransferrin, lysozyme, casein, beta-lactoglobulin, alpha-lactoalbumin, alpha-amylase inhibitor and glyadine) and their heated preparations were absorbed to the membrane, which was blocked with 3% RSA-added TBS and washed with TBST. The antibodies against egg-allergen fraction, milk-allergen fraction and wheat-allergen fraction (diluted 2000-fold) were added to the membrane and allowed to stand for 1 h at room temperature. Subsequently, biotin-conjugated anti-rabbit IgG sheep antibody and HRP-conjugated avidin (4000-fold) were added to the membrane, which was washed and subjected to determination of photons generated by the reaction with a chemiluminescent reagent and trapped on a photosensitive film.

The above-mentioned antibodies detected the major allergens of ovoalbumin, ovomucoid, ovotransferrin, lysozyme, casein, beta-lactoglobulin, alpha-lactoalbumin, alpha-amylase inhibitor and glyadine. The antibodies detected the heated preparations of the above-mentioned purified allergens, too.

Example 6

Detection of Egg, Milk and Wheat Allergens by Sandwich ELISA (1) Antibodies Antibodies against the allergen fractions of egg, milk and wheat prepared in Example 4 (4), and those conjugated with biotin prepared according to the conventional manner were used in the following.

(2) Coating and Blocking of the Antibodies on a Microtiter Plate

A 100-μl portion of the above-mentioned antibodies (10 μg/ml) was dispensed in wells of an ELISA plate (Nunc), allowed to stand at 4 degree Celsius overnight, washed (150 mM-NaCl and 0.05% Tween 20-added 20 mM Tris-HCl buffer, pH 7.4), and blocked with 0.1% RSA (Sigma) for 1 h at 25 degree Celsius.

(3) Detection of Egg, Milk and Wheat Allergens

After the blocking solution in the wells was removed, 95-μl portion of diluent (0.1%-RSA, 150 mM-NaCl and 0.05% Tween 20-added 20 mM Tris-HCl buffer, pH 7.4) and 5-μl portion of PBS extract from various foods were added to the wells and allowed to stand for 2 h at 25 degree Celsius. Similarly, 5-μl portion of suspension of the egg, milk and wheat standard antigens mentioned in Example 1 was added to the wells and allowed to stand for 2 h at 25 degree Celsius. After 5-time washing with 300 μl washing liquid, a 100-μl portion of biotin-conjugated antibody (10000-fold dilution) was added to the wells and allowed to stand for 1 h at 25 degree Celsius, and then a 100-μl portion of peroxidase-conjugated avidin (2500-fold dilution) was added to the wells and allowed to stand for 30 min at 25 degree Celsius. After washing, a 100-μl portion of 3,3',5,5'-tetrabenzidine solution was added to the wells and allowed to react for 30 min at 25 degree Celsius under light shielding. Then, a 100-μl portion of 1 N sulfuric acid was added to stop the reaction. Optical densities of the wells were read by a microtiterplate reader (at 450 nm of a main wavelength and at 630 nm of a sub wavelength).

The results are shown in Table 1. As Table 1 shows, the egg, milk and wheat allergens in various food extracts could be detected.

TABLE 1

Detection of egg, milk and wheat in various foods

| Food | Antibody against egg-allergen fraction | Antibody against milk-allergen fraction | Antibody against wheat-allergen fraction |
|---|---|---|---|
| Boiled egg | ○ | X | X |
| Milk | X | ○ | X |
| Bread (prepared in the laboratory) | X | X | ○ |
| Pudding (prepared in the laboratory with egg and milk) | ○ | ○ | X |
| French toast (prepared in the laboratory with egg, milk and wheat) | ○ | ○ | ○ |

○; Detected.
X; Not detected. (Similar in the following tables)

Example 7

Evaluation of Fundamental Property of the Food Allergen-Detection Kit by the Sandwich ELISA Method (1) Dilution Test of the Standard Antigen According to Example 6, the egg, milk and wheat standard antigens prepared in Example 1 were quantified. Plotting these results on sheets of plotting paper, calibration curves approximately running through origins could be obtained.

(2) Evaluation of Reproducibility among Simultaneous Assays

According to the above-mentioned method, samples A to E of the egg standard antigen of five different concentrations within a detectable range were prepared and subjected to five simultaneous assays. As shown in Table 2, a CV value of lower than 5% was obtained. Thus, an excellent simultaneous reproducibility was confirmed.

TABLE 2

Evaluation of reproducibility among simultaneous assays of egg standard-antigen detection by the sandwich ELISA method

| | 1 | 2 | 3 | 4 | 5 | Mean | SD | CV(%) |
|---|---|---|---|---|---|---|---|---|
| A | 1.165 | 1.079 | 1.068 | 1.075 | 1.064 | 1.090 | 0.042 | 3.87 |
| B | 0.756 | 0.711 | 0.699 | 0.689 | 0.693 | 0.710 | 0.027 | 3.84 |
| C | 0.544 | 0.505 | 0.500 | 0.497 | 0.507 | 0.511 | 0.019 | 3.74 |
| D | 0.233 | 0.222 | 0.236 | 0.222 | 0.227 | 0.228 | 0.006 | 2.79 |
| E | 0.175 | 0.165 | 0.179 | 0.173 | 0.170 | 0.172 | 0.005 | 3.06 |

(3) Evaluation of Reproducibility Among Day-to-Day Assays

According to the above-mentioned method, samples A to E of the milk standard antigen of five different concentrations within a detectable range were prepared and subjected to 5 successive-day assays. As shown in Table 3, a CV value of lower than 5% was obtained. Thus, an excellent reproducibility among day-to-day assays was confirmed.

TABLE 3

Evaluation of reproducibility among day-to-day assays of milk standard-antigen detection by the sandwich ELISA method

| | 1 | 2 | 3 | 4 | 5 | Mean | SD | CV(%) |
|---|---|---|---|---|---|---|---|---|
| A | 2.356 | 2.387 | 2.346 | 2.321 | 2.241 | 2.330 | 0.055 | 2.37 |
| B | 1.353 | 1.306 | 1.274 | 1.246 | 1.254 | 1.287 | 0.044 | 3.40 |
| C | 0.956 | 0.949 | 0.928 | 0.921 | 0.899 | 0.931 | 0.023 | 2.45 |
| D | 0.295 | 0.292 | 0.275 | 0.281 | 0.278 | 0.284 | 0.009 | 3.10 |
| E | 0.195 | 0.183 | 0.186 | 0.184 | 0.182 | 0.186 | 0.005 | 2.82 |

These results show that the present method can rapidly and stably detect multiple native and denatured food allergens distributed in foods and their ingredients. It was confirmed that the method could detect 0.5 ng/ml or more of the food allergen or the food allergen-containing food.

Example 8

Food-Allergy Patients are Carrying IgE Antibodies Against Both Native and Heated Food Allergens Taking egg allergy for instance, it was confirmed that the food-allergy patients were carrying IgE antibodies against not only native but also heated food allergen. Namely, whole egg (non-heated egg antigen) was dissolved in PBS (1.0%, w/v). Half volume of the solution was heated for 30 min at 120 degree Celsius (heated egg antigen). A 100-μl portion of each 10-fold diluted solution was dispensed on an ELISA plate, which was coated, washed, blocked with 1% HAS-added PBS and washed. Thus, the native egg antigen-coated plate and the heated egg antigen-coated plate were prepared.

Next, either the native egg antigen or the heated egg antigen (1, 5, 50, 100, 500 and 1000 ng/ml) was added to the pooled patients' serum described in Example 4 (1) (1000-fold dilution), reacted for 2 h at 37 degree Celsius, and centrifuged. Thus, two kinds of the serum were prepared. The former and the latter were named the native egg antigen-depleted serum and the heated egg antigen-depleted serum, respectively.

Then, each 100-μl portion of either the native egg antigen-depleted serum and the heated egg antigen-depleted serum was dispensed on each of the native egg antigen-coated plate and the heated egg antigen-coated plate, which were allowed to stand for 2 h at 37 degree Celsius and washed with PBST. A 100-μl portion of biotin-conjugated anti-human IgE-ε goat antibody (2500-fold dilution) was added to the plates, which were allowed to stand for 1 h at 37 degree Celsius and washed with PBST. After addition of alkaline phosphatase-conjugated avidin (standing for 30 min at 37 degree Celsius) and a luminescent substrate, degrees of luminescence were read (Luminometer CT-9000D, Diatron). The results are shown in FIG. 2.

As shown in FIG. 2, it was confirmed that the heated egg antigen-depleted serum (shown as ○ in FIG. 2) could specifically react with the native egg antigen (the left figure of FIG. 2), but that the serum could do with the heated antigen (the right figure of FIG. 2). Meanwhile, it was confirmed that the native egg antigen-depleted serum (shown as ● in FIG. 2) could specifically react with the heated egg antigen (the right figure of FIG. 2), but that the serum could do with the native antigen (the left figure of FIG. 2).

From these results, it was proved that the food-allergy patients were carrying IgE antibodies specifically recognizing both the native and the heated egg.

Therefore, a method for detecting a food allergen should be able to detect both the heated and the native allergen.

Example 9

Enhancement of ELISA Intensity with Antibody Prepared by Immunization of a Heated Antibody Even if the anti-allergen fraction antibody as described in Example 4 is subjected to the determination, ELISA intensity (optical density, OD value) obtained by a reaction between the antibody and a heated sample may be lower than that obtained by the reaction between the antibody and a native one. This may depend upon (1) that protein concentration of the extract from the heated sample is lower than that from the native one; and (2) that reactivity between the heated sample and the antibody is lower than that between the native one and the antibody, even if a protein concentration of the samples is evenly adjusted. Consequently, preparation of the antibody with enhanced reactivity was studied.

The egg allergen fraction as described in Example 4 (1) was autoclaved for 30 min at 120 degree Celsius, cooled, homogenized with 4 M urea-added PBS, and centrifuged. The supernatant was freeze-dried and finely ground to prepare the antigen, which was subjected to preparation of the rabbit antibody (hereinafter, anti-autoclaved egg antigen antibody) as described in Example 3 (1). According to the method as described in Example 6, the antibody was subjected to reaction with the native egg antigen-coated plate and the heated egg antigen-coated plate as described in Example 8.

These results are shown in Table 4. Table 4 shows that the native and heated egg antigens were detected with the almost same ELISA intensities by using the antibody prepared by immunization of the extract from the autoclaved food allergen. Thus, above-mentioned problems were solved.

TABLE 4

Enhancement of ELISA intensity with antibody prepared by immunization of a heated antibody

| Antibody | ELISA intensity | |
|---|---|---|
| | Native egg antigen-coated plate | Heated egg antigen-coated plate |
| Anti-egg allergen fraction antibody | 100 | 36 |
| Anti-autoclaved egg antigen antibody | 100 | 118 |

ELISA intensity (OD value) obtained by a reaction between the anti-egg allergen fraction antibody and the standard egg-antigen plate is shown as 100.

Example 10

Determination of the Food Allergens and the Food Allergy-Inducing Foods-1

Whether the multiple antigen-recognizing antibodies of this invention (those as described in Example 3) and the method as described in Example 7 could detect food allergen-containing foods or not was examined. Using a calibration curve prepared as described in Example 7, quantification was carried out and quantification indexes (measured value/actual value×100) were calculated. Results from egg yolk, egg white, egg-yolk mayonnaise and whole-egg mayonnaise are shown in Table 5.

When the antibody prepared from a single antigen localizing in the egg white was subjected to the determination, Table 5 shows that (1) no egg yolk but egg white could be detected, and that (2) the standard egg antigen's measured value from the calibration curve was twice to 60-times more than the actual value.

When the multiple antigen-recognizing anti-standard egg antigen antibodies of this invention were subjected to the determination, Table 5 shows that (3) both egg yolk and egg white could be detected, and that (4) measured value of the standard egg antigen was almost the same as the actual value. From these results, it was noticed that the anti-standard egg antigen antibody recognizing the multiple antigens of this invention could detect and quantify an allergy-inducing food of egg or its ingredient in egg-processed food.

TABLE 5

Possibility of detection and/or quantification of egg and egg products with various antibodies

| Sample | Determination | Multiple antigen-recognizing antibody (Anti-standard egg antigen antibody) | Single antigen-recognizing antibody (Anti-ovomucoid antibody) | Single antigen-recognizing antibody (Anti-ovoalbumin antibody) |
|---|---|---|---|---|
| Egg yolk | Possibility of detection | ○ | X | X |
| | Quantification index | 74-106 | | |
| Egg white | Possibility of detection | ○ | ○ | ○ |
| | Quantification index | 105-170 | 240-310 | 6,330-13,150 |
| Egg-yolk mayonnaise | Possibility of detection | ○ | X | X |
| Whole-egg mayonnaise | Possibility of detection | ○ | ○ | ○ |

Example 11

Determination of the Food Allergens and the Food Allergy-Inducing Foods-2

Milk whey, casein, lactoferrin, and casein hydrolysate were examined as mention in Example 10. The results are shown in Table 6.

Table 6 shows that (1) anti-standard milk antigen antibody recognizing the multiple antigen of this invention could detect and quantify the food allergy-inducing milk and its ingredients; but that (2) a single antigen recognizing antibody prepared by immunization of a substance localizing in the milk whey could not quantify them. Symbol of Δ in Table 6 shows that quantification could be accomplished but that the quantification index was below 5.

TABLE 6

Possibility of detection and/or quantification of the standard milk antigen with various antibodies

| Sample | Determination | Multiple antigen-recognizing antibody (Anti-standard milk antigen antibody) | Single antigen-recognizing antibody (Anti-casein antibody) | Single antigen-recognizing antibody (Anti-beta lactoglobulin antibody) |
|---|---|---|---|---|
| Milk whey | Possibility of detection | ○ | X | ○ |
|  | Quantification index | 160-230 |  | 320-1,080 |
| Casein | Possibility of detection | ○ | ○ | X |
|  | Quantification index | 38-47 | 170-180 |  |
| Lactoferrin | Possibility of detection | ○ | Δ | X |
| Casein hydrolysate | Possibility of detection | ○ | X | Δ |

The invention claimed is:

1. An isolated polyclonal rabbit serum antibody mixture comprising multiple different antibodies specifically recognizing different native and denatured egg allergens, wherein the different egg allergens are in food selected from the group consisting of native and heat denatured homogenized, freeze-dried and ground chicken eggs, native and heat denatured homogenized, freeze-dried and ground quail eggs, and native and heat denatured homogenized, freeze-dried and ground duck eggs and wherein said isolated polyclonal rabbit serum antibody mixture does not recognize any allergens, which are not also specifically recognized by IgE antibodies of egg allergy patients as an ingested egg allergen that causes egg allergy.

2. The mixture of antibodies of claim 1, wherein the egg allergens are ovalbumin, ovomucoid, lysozyme and ovotransferrin of egg.

3. The isolated antibody mixture of claim 1, wherein the egg allergy patient has an allergy to ingested egg allergens and a radioallergosorbent test (RAST) score of 2 or more, wherein said RAST test score indicates the level of egg allergen specific IgE antibodies in said patient.

4. The isolated antibody mixture of claim 1, wherein the isolated polyclonal antibody mixture can specifically bind to egg allergens found in food, and thereby detect the presence of egg allergens in food by immunoassay.

5. The isolated antibody mixture of claim 4, wherein said immunoassay is ELISA.

6. The isolated polyclonal rabbit serum antibody mixture of claim 1, wherein the antibody mixture specifically recognizes all of: a) a native and denatured form of ovoalbumin; b) a native and denatured form of ovomucoid of egg; c) a native and denatured form of egg lysozyme.

7. The isolated polyclonal rabbit serum antibody mixture according to claim 1, wherein the isolated polyclonal rabbit serum antibody mixture is prepared by:

a) isolating IgE antibodies from a pooled serum of egg-allergy patients, wherein the egg allergy patients have allergies to ingested egg allergens;

b) preparing a profile of the different native and denatured egg allergens of claim 1 that the IgE antibodies from step a) specifically recognize;

c) immunizing a rabbit with the different native and denatured egg allergens to obtain a rabbit serum antibody mixture;

d) preparing a profile of egg allergens that the rabbit serum antibodies from step c) specifically recognize;

e) comparing the profiles of step b and step c;

f) collecting the different native and denatured egg allergens which are specifically recognized by the IgE antibodies and the rabbit serum antibody mixture;

g) immunizing a rabbit with the different native and denatured egg allergens from step f), thereby obtaining the isolated polyclonal rabbit serum antibody mixture of claim 1.

8. An isolated polyclonal rabbit serum antibody mixture comprising multiple different antibodies specifically recognizing different native and denatured milk allergens, wherein the different milk allergens are in native and heat denatured filtered, freeze-dried and ground cow's milk and wherein said isolated polyclonal rabbit serum antibody mixture does not recognize any allergens, which are not also specifically recognized by IgE antibodies of milk allergy patients as an ingested milk allergen that causes milk allergy.

9. The mixture of antibodies of claim 8, wherein the milk allergens are casein, beta-lactoglobulin and alpha-lactoalbumin of milk.

10. The isolated antibody mixture of claim 8, wherein the milk allergy patient has an allergy to ingested milk allergens and a radioallergosorbent test (RAST) score of 2 or more, wherein said RAST test score indicates the level of milk allergen specific IgE antibodies in said patient.

11. The isolated antibody mixture of claim 8, wherein the isolated polyclonal antibody mixture can specifically bind to milk allergens found in food, and thereby detect the presence of milk allergens in food by immunoassay.

12. The isolated antibody mixture of claim 11, wherein said immunoassay is ELISA.

13. The isolated polyclonal rabbit serum antibody mixture according to claim 8, wherein the isolated polyclonal rabbit serum antibody mixture is prepared by:

a) isolating IgE antibodies from a pooled serum of milk-allergy patients, wherein the milk allergy patients have allergies to ingested milk allergens;

b) preparing a profile of the different native and denatured milk allergens of claim 8 that the IgE antibodies from step a) specifically recognize;

c) immunizing a rabbit with the different native and denatured milk allergens to obtain a rabbit serum antibody mixture;

d) preparing a profile of milk allergens that the rabbit serum antibodies from step c) specifically recognize;

e) comparing the profiles of step b and step c;

f) collecting the different native and denatured milk allergens which are specifically recognized by the IgE antibodies and the rabbit serum antibody mixture;

g) immunizing a rabbit with the different native and denatured milk allergens from step f), thereby obtaining the isolated polyclonal rabbit serum antibody mixture of claim 8.

14. An isolated polyclonal rabbit serum antibody mixture comprising multiple different antibodies specifically recognizing different native and denatured wheat allergens, wherein the different wheat allergens are in native and heat denatured dialyzed, freeze-dried and ground wheat and wherein said isolated polyclonal rabbit serum antibody mixture does not recognize any allergens, which are not also specifically recognized by IgE antibodies of wheat allergy patients as an ingested wheat allergen that causes wheat allergy.

15. The mixture of antibodies of claim 14, wherein the wheat allergens are gliadin and alpha-amylase inhibitor of wheat.

16. The isolated antibody mixture of claim 14, wherein the wheat allergy patient has an allergy to ingested wheat allergens and a radioallergosorbent test (RAST) score of 2 or more, wherein said RAST test score indicates the level of wheat allergen specific IgE antibodies in said patient.

17. The isolated antibody mixture of claim 14, wherein the isolated polyclonal antibody mixture can specifically bind to wheat allergens found in food, and thereby detect the presence of wheat allergens in food by immunoassay.

18. The isolated antibody mixture of claim 17, wherein said immunoassay is ELISA.

19. The isolated polyclonal rabbit serum antibody mixture according to claim 14, wherein the isolated polyclonal rabbit serum antibody mixture is prepared by:
    a) isolating IgE antibodies from a pooled serum of wheat-allergy patients, wherein the wheat allergy patients have allergies to ingested wheat allergens;
    b) preparing a profile of the different native and denatured wheat allergens of claim 14 that the IgE antibodies from step a) specifically recognize;
    c) immunizing a rabbit with the different native and denatured wheat allergens to obtain a rabbit serum antibody mixture;
    d) preparing a profile of wheat allergens that the rabbit serum antibodies from step c) specifically recognize;
    e) comparing the profiles of step b and step c;
    f) collecting the different native and denatured wheat allergens which are specifically recognized by the IgE antibodies and the rabbit serum antibody mixture;
    g) immunizing a rabbit with the different native and denatured wheat allergens from step f), thereby obtaining the isolated polyclonal rabbit serum antibody mixture of claim 14.

20. An isolated polyclonal rabbit serum antibody mixture comprising multiple different antibodies specifically recognizing different native and denatured buckwheat allergens,
    wherein the different buckwheat allergens are in native and heat denatured dialyzed, freeze-dried and ground buckwheat
    and wherein said isolated polyclonal rabbit serum antibody mixture does not recognize any allergens, which are not also specifically recognized by IgE antibodies of buckwheat-allergy patients as an ingested buckwheat allergen that causes buckwheat allergy.

21. The mixture of antibodies of claim 20, wherein the buckwheat allergens are buckwheat substances of 132-, 84-, 27-, and 11-kDa molecular weight
    wherein the molecular weights are determined by sodium dodecyl sulfate polyacrylamide gel electrophoresis, under reducing conditions.

22. The isolated antibody mixture of claim 20, wherein the buckwheat allergy patient has an allergy to ingested buckwheat allergens and a radioallergosorbent test (RAST) score of 2 or more, wherein said RAST test score indicates the level of buckwheat allergen specific IgE antibodies in said patient.

23. The isolated antibody mixture of claim 20, wherein the isolated polyclonal antibody mixture can specifically bind to buckwheat allergens found in food, and thereby detect the presence of buckwheat allergens in food by immunoassay.

24. The isolated antibody mixture of claim 23, wherein said immunoassay is ELISA.

25. The isolated polyclonal rabbit serum antibody mixture according to claim 20, wherein the isolated polyclonal rabbit serum antibody mixture is prepared by:
    a) isolating IgE antibodies from a pooled serum of buckwheat-allergy patients, wherein the buckwheat allergy patients have allergies to ingested buckwheat allergens;
    b) preparing a profile of the different native and denatured buckwheat allergens of claim 20 that the IgE antibodies from step a) specifically recognize;
    c) immunizing a rabbit with the different native and denatured buckwheat allergens to obtain a rabbit serum antibody mixture;
    d) preparing a profile of buckwheat allergens that the rabbit serum antibodies from step c) specifically recognize;
    e) comparing the profiles of step b and step c;
    f) collecting the different native and denatured buckwheat allergens which are specifically recognized by the IgE antibodies and the rabbit serum antibody mixture;
    g) immunizing a rabbit with the different native and denatured buckwheat allergens from step f), thereby obtaining the isolated polyclonal rabbit serum antibody mixture of claim 20.

26. An isolated polyclonal rabbit serum antibody mixture comprising multiple different antibodies specifically recognizing different native and denatured peanut allergens,
    wherein said different peanut allergens are in heat denatured and native dialyzed, freeze-dried and ground peanut
    and wherein said isolated polyclonal rabbit serum antibody mixture does not recognize any allergens, which are not also specifically recognized by IgE antibodies of peanut-allergy patients as an ingested peanut allergen that causes peanut allergy.

27. The mixture of antibodies of claim 26, wherein the peanut allergens are peanut substances of 107-, 72-, 35-, and 28-kDa in molecular weight
    and wherein the molecular weight of the peanut allergens is determined by sodium dodecyl sulfate polyacrylamide gel electrophoresis, under reducing conditions.

28. The isolated antibody mixture of claim 26, wherein the peanut allergy patient has an allergy to ingested peanut allergens and a radioallergosorbent test (RAST) score of 2 or more, wherein said RAST test score indicates the level of peanut allergen specific IgE antibodies in said patient.

29. The isolated antibody mixture of claim 26, wherein the isolated polyclonal antibody mixture can specifically bind to peanut allergens found in food, and thereby detect the presence of peanut allergens in food by immunoassay.

30. The isolated antibody mixture of claim 29, wherein said immunoassay is ELISA.

31. The isolated polyclonal rabbit serum antibody mixture according to claim 26, wherein the isolated polyclonal rabbit serum antibody mixture is prepared by:
    a) isolating IgE antibodies from a pooled serum of peanut-allergy patients, wherein the peanut allergy patients have allergies to ingested peanut allergens;
    b) preparing a profile of the different native and denatured peanut allergens of claim 26 that the IgE antibodies from step a) specifically recognize;
    c) immunizing a rabbit with the different native and denatured peanut allergens to obtain a rabbit serum antibody mixture;
    d) preparing a profile of peanut allergens that the rabbit serum antibodies from step c) specifically recognize;
    e) comparing the profiles of step b and step c;

f) collecting the different native and denatured peanut allergens which are specifically recognized by the IgE antibodies and the rabbit serum antibody mixture;

g) immunizing a rabbit with the different native and denatured peanut allergens from step f), thereby obtaining the isolated polyclonal rabbit serum antibody mixture of claim 26.

32. An isolated polyclonal rabbit serum antibody mixture comprising multiple different antibodies specifically recognizing different native and denatured rice allergens, wherein said different rice allergens are in native and heat denatured dialyzed, freeze-dried and ground rice and wherein said isolated polyclonal rabbit serum antibody mixture does not recognize any allergens, which are not also specifically recognized by IgE antibodies of rice allergy patients as an ingested rice allergen that causes rice allergy.

33. The isolated polyclonal rabbit serum antibody mixture according to claim 32, wherein the isolated polyclonal rabbit serum antibody mixture is prepared by:

a) isolating IgE antibodies from a pooled serum of rice-allergy patients, wherein the rice allergy patients have allergies to ingested rice allergens;

b) preparing a profile of the different native and denatured rice allergens of claim 32 that the IgE antibodies from step a) specifically recognize;

c) immunizing a rabbit with the different native and denatured rice allergens to obtain a rabbit serum antibody mixture;

d) preparing a profile of rice allergens that the rabbit serum antibodies from step c) specifically recognize;

e) comparing the profiles of step b and step c;

f) collecting the different native and denatured rice allergens which are specifically recognized by the IgE antibodies and the rabbit serum antibody mixture;

g) immunizing a rabbit with the different native and denatured rice allergens from step f), thereby obtaining the isolated polyclonal rabbit serum antibody mixture of claim 32.

34. An isolated polyclonal rabbit antibody serum mixture comprising multiple different antibodies specifically recognizing different native and denatured soybean allergens, wherein said different soybean allergens are in native and heat denatured dialyzed, freeze-dried and ground soybean and wherein said isolated polyclonal rabbit serum antibody mixture does not recognize any allergens, which are not also specifically recognized by IgE antibodies of soybean allergy patients as an ingested soybean allergen that causes soybean allergy.

35. The isolated polyclonal rabbit serum antibody mixture according to claim 34, wherein the isolated polyclonal rabbit serum antibody mixture is prepared by:

a) isolating IgE antibodies from a pooled serum of soybean-allergy patients, wherein the soybean allergy patients have allergies to ingested soybean allergens;

b) preparing a profile of the different native and denatured soybean allergens of claim 34 that the IgE antibodies from step a) specifically recognize;

c) immunizing a rabbit with the different native and denatured soybean allergens to obtain a rabbit serum antibody mixture;

d) preparing a profile of soybean allergens that the rabbit serum antibodies from step c) specifically recognize;

e) comparing the profiles of step b and step c;

f) collecting the different native and denatured soybean allergens which are specifically recognized by the IgE antibodies and the rabbit serum antibody mixture;

g) immunizing a rabbit with the different native and denatured soybean allergens from step f), thereby obtaining the isolated polyclonal rabbit serum antibody mixture of claim 34.

* * * * *

UNITED STATES PATENT AND TRADEMARK OFFICE
CERTIFICATE OF CORRECTION

| | |
|---|---|
| PATENT NO. | : 8,361,460 B2 |
| APPLICATION NO. | : 10/488461 |
| DATED | : January 29, 2013 |
| INVENTOR(S) | : Fumiki Morimatsu et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 224 days.

Signed and Sealed this
Eighteenth Day of November, 2014

Michelle K. Lee
*Deputy Director of the United States Patent and Trademark Office*